US006239286B1

(12) United States Patent
Kis-Tamás et al.

(10) Patent No.: US 6,239,286 B1
(45) Date of Patent: May 29, 2001

(54) PROCESS FOR THE PREPARATION OF 1,3-DIAZA-SPIRO (4.4) NON-1-EN-4-ONE DERIVATIVES AND 1-CYANO-1-ACYLAMINO-CYCLOPENTANE INTERMEDIATES

(75) Inventors: Attila Kis-Tamás; Csaba Huszár, both of Budapest (HU); Bertrand Castro, Aunes (FR); Attila Németh, Göd (HU); Péter Aranyosi, Budapest (HU); Károly Gyüre, Dunakeszi (HU); István Mészáros, Budapest (HU); Ilona Dervalicsné Zrínyi, Budapest (HU); Katalin Dubovszki, Budapest (HU); Lajosné Páli, Budapest (HU); Antal Gajáry, Budapest (HU); Attila Supic, Budapest (HU); Zsuzsanna Nád, Budapest (HU); Zoltán Makovi, Budapest (HU); Endre Kollár, Budapest (HU); Zsuzsanna Csetriné Hári, Budapest (HU); Ágnes Kunsztné Kárász, Budapest (HU); Erzsébet Bognár, Budapest (HU)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/463,434

(22) PCT Filed: Jul. 22, 1998

(86) PCT No.: PCT/HU98/00067

§ 371 Date: May 15, 2000

§ 102(e) Date: May 15, 2000

(87) PCT Pub. No.: WO99/05119

PCT Pub. Date: Feb. 4, 1999

(30) Foreign Application Priority Data

Jul. 25, 1997 (HU) .................................................. 97 01294

(51) Int. Cl.[7] ................................................ C07D 235/02
(52) U.S. Cl. ...................................... 548/316.4; 558/432
(58) Field of Search ........................... 558/432; 548/316.4

(56) References Cited

U.S. PATENT DOCUMENTS

| 5,541,209 | 7/1996 | Spinale ................................. 514/381 |
| 5,698,704 | * 12/1997 | Jackson .......................... 548/316.4 X |
| 5,910,595 | * 6/1999 | Durrwachter ................. 548/316.4 X |
| 6,037,474 | * 3/2000 | Drauz et al. ...................... 548/316.4 |

FOREIGN PATENT DOCUMENTS

| A1 532410 | 3/1993 | (EP) . |
| A1 789019 | 8/1997 | (EP) . |
| WO 91 14679 | 10/1991 | (WO) . |
| WO 96 38406 | 5/1996 | (WO) . |
| WO 97 36868 | 9/1997 | (WO) . |

OTHER PUBLICATIONS

Granger et al., Séance Du, vol. 250, No. 2, Apr. 4, 1960, pp. 2581–2583.
Sudo et al., Bulletin of the Chemical Society of Japan, vol. 36, No. 1, pp. 34–37, 1963.
Bernhart et al., Journal of Medicinal Chemistry, vol. 36, No. 22, 1993, pp. 3371–3380.
O'Brien et al., Journal of Medicinal Chemistry, vol. 37, No. 12, 1994, pp. 1810–1822.
Takenaka et al., Heterocycles, vol. 29, No. 6, 1989 pp. 1185–1189.
Bruckner, Szerves Kemisa, vol. III–1, 1964, p. 296.
Allen et al., Organic Syntheses, vol. 3, 1955, pp. 66–69, 84–86, 88–90.

* cited by examiner

*Primary Examiner*—Fiona T. Powers
(74) *Attorney, Agent, or Firm*—Birch, Stewart, Kolasch & Birch, LLP

(57) ABSTRACT

Process for the preparation of compounds of formula (I) wherein R means hydrogen atom, or $C_{1-6}$ alkyl group, or $C_{7-12}$ aralkyl group or phenyl group, characterised in that: a) the compound of formula (III) is reacted with a compound of formula (IV) wherein X means halogen atom or $C_{1-5}$ alkoxy group or hydroxyl group and the resulting compound of formula (II) is transformed in the presence of an oxidising agent in a reaction medium with pH above 7, into the compound of formula (I), or b) the compound of formula (III) is reacted with an anhydride of general formula (V) and the resulting compound of formula (II) transformed in the presence of an oxidising agent, in a reaction medium with pH above 7, into the compound of formula (I), or c) a compound of formula (II) is transformed in the presence of an oxidising agent, in a reaction medium with pH above 7, into the compound of formula (I), and if desired, the resulting compounds of formula (I), before or after isolation, are transformed into acid addition salts, or the compounds of formula (I) are liberated from their acid addition salts. Thus a process for the preparation of intermediates useful in synthesis of angiotensin II antagonists is disclosed.

12 Claims, 1 Drawing Sheet

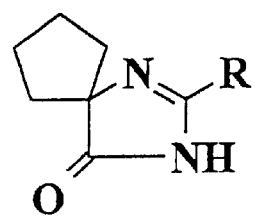  (I)
  (II)
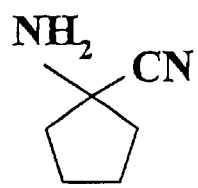  (III)
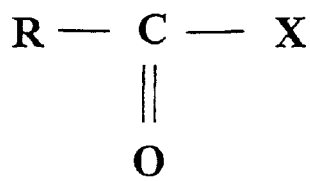  (IV)
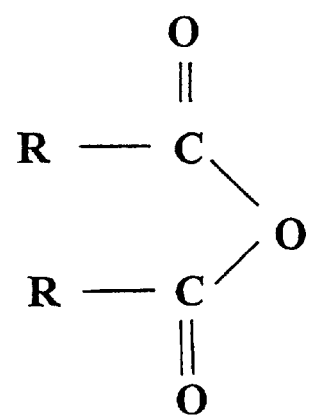  (V)

PROCESS FOR THE PREPARATION OF 1,3-DIAZA-SPIRO (4.4) NON-1-EN-4-ONE DERIVATIVES AND 1-CYANO-1-ACYLAMINO-CYCLOPENTANE INTERMEDIATES

This application is the national phase under 35 U.S.C. §371 of PCT International Applcation No. PCT/HU98/00067 which has an International filing date of Feb. 4, 1999, which designated the United States of America.

This invention relates to the new process for the preparation of compounds of general formula (I)—wherein R means hydrogen atom or $C_{2-6}$ alkyl group—and to the intermediates of general formula (II)—wherein the meaning of R is the same as above. Compounds of general formula (I) are important intermediates used in the course of preparation of active components of pharmaceuticals. They are e.g. applied in the synthesis of angiotensine II antagonists (PCT application, publication number WO-91/14679A).

Synthesis of 4-imidazolinones and their 2-substituted derivatives, constituting the main skeleton of compounds of general formula (I) is known from the literature (Bruckner: Szerves kémia Band III-1 page 296. Edition: Tankönyvkiad ó, Budapest 1964). Takenaka and his co-workers described the preparation of 2-phenyl-4,4'-dialkyl-5-oxo-2-imidazolines in tetrahydrofuran-water heterogeneous system by a 5-12 hours reflux/Heterocycles 29 (6) p 1185 (1989)/. The above method is, however, difficult to implement since preparation of the appropriate carboxamides is problematic. The appropriate carboxamides are in general synthetised by partial hydrolysis of α-aminonitriles, thus, by that of the α-aminonitrile (II). Taking into account the sensitivity of the aminonitriles against alkalines and oxidants, from the known methods only the partial hydrolysis performed in concentrated acidic medium is considered as feasible.

The transformation of nitriles into carboxamides in strongly acidic medium, preferably in concentrated sulfuric acid, raises, however, a number of problems. To be able to stir the reaction mixture, sulfuric acid has to be applied in large excess. As a consequence, heating up the reaction mixture to 70° C. and cooling it down takes considerable time and keeping the reaction product for longer time in a concentrated sulfuric acidic medium will cause partial decomposition. This will cause the necessity of further purification steps. Since the aminocarboxamides are obtained in the form of sulfate salts, the amides have to be liberated. Neutralization of the large excess of acid means the addition of large amounts of base and also that of water, in order to keep the resulting salt in solution. The aminocarboxamide obtained is well solvated, its extraction from the reaction mixture requires a minimum 40-fold excess of the extracting solvent, even if the best—but from the aspect of health very unfavourable—chlorinated hydrocarbones are applied. These solvents, at that, can be recovered only with high losses.

Our aim was to work out a novel process for the preparation of the compounds of a general formula (I) eliminating the above problems.

We have found that if a) the compound of formula (III) is reacted with a compound of general formula (IV)—wherein R means hydrogen atom or $C_{2-6}$ alkyl group, X means halogen atom, $C_{1-5}$ alkoxy group or hydroxyl group—and the resulting compound of general formula (II)—wherein the meaning of R is the same as given above—is transformed, in the presence of an oxidizing agent in a reaction medium with pH above 7, into the compound of general formula (I)—wherein the meaning of R is as defined above—, or b) the compound of formula (III) is reacted with an anhydride of general formula (V)—wherein the meaning of R is the same as defined above—, and the resulting compound of general formula (II)—wherein the meaning of R is as given above—is transformed in the presence of an oxidizing agent, in a reaction medium with pH above 7, into the compound of general formula (I), or c) a compound of general formula (II)—wherein the meaning of R is the same as defined above—is transformed in the presence of an oxidizing agent, in a reaction medium with pH above 7, into the compound of general formula (I), and, if desired, the resulting compounds of general formula (I), before or after isolation, are transformed into acid addition salts, or the compounds of general formula (I) are liberated from their acid addition salts, then the disadvantages of the known methods are avoided and the new method is also suitable for the "one-pot" synthesis of the compounds of general formula (I).

In the first, acylation step the use of acid chlorides is the most advantageous, in the presence of an organic solvent and an acid binding agent. As for organic solvents for example ethers (methyl tert.-butyl ether), aromatic hydrocarbones e.g. toluene, xylene or chlorinated hydrocarbones e.g. dichloroethane can be applied, as for acid binding agents inorganic bases, for example alkali metal carbonates, alkali-earth metal oxides, organic bases e.g. trialkylamines may be employed.

The resulting, if desired isolated, compounds of general formula (II) are new, they are not known from the literature.

Transformation of the compounds of general formula (II) was carried out in the presence of the above solvents or of alcohols, preferably by use of hydrogen peroxide, but other oxidising agents can also facilitate the reaction. Reactions performed in water-organic solvent mixtures may be accelerated by use of dissolution transfer, phase transfer catalyst or by intensive stirring. As phase transfer catalyst preferably substituted ammonium salts, as for example tetrabutyl ammonium hydroxides, hydrogen halogenides, hydrogen sulfates, as well as other ammonium derivatives containing equal or different subsituents can also be applied. The reaction is carried out in basic medium, above pH=7, for instance in the presence of sodium hydroxide, but other alkali metal hydroxides, as well as alkali metal carbonates, alkali-earth metal hydroxides, alkali-earth metal carbonates or anion-exchange resins may also be used.

Cyclisation may be accomplished in 0.5–2 hours.

The cyclisation step is preferably carried out at a temperature between 50–160° C. The whole process can be carried out in one reaction pot and the resulting compounds of general formula (I) contain, at the highest. 0.1% amount of contamination. The yield of the process is over 70%, calculated on the starting compound of formula (III). The compounds of general formula (I) are preferably isolated in the form of their organic or inorganic acid addition salts. Synthesis of the starting compound of formula (III) is known from the literature/it was synthetised according to the method of the PCT application, publ. number WO-91/14679 and of Org. Synt. 1955 3; (MS: (m/z) 110, 95, 81, 68, 54, 41, 28)/.

Further details of the invention are illustrated by the following examples.

EXAMPLE 1

1-cyano-1-n-pentanoylaminocyclopentane

To 11.0 g (0.1 mol) of 1-amino-1-cyanocyclopentane dissolved in 100 ml of dichloromethane, 15 ml 10.9 g (0.1 mol) of triethylamine was added, then dropwise 13 ml, 13 g (0.1 mol) of valeroyl chloride, while keeping the temperature at 25–35° C. The reaction mixture was stirred at 30–35° C. for 2 hours, then it was washed with water. The phases were separated, the organic phase was evaporated to obtain the pure title compound as an oil. The compound was identified by elementary analysis, IR, NMR and GC-MS spectomety.

$^1$H-NMR (CDCl$_3$): δ 0.81 (CH$_3$); 1.25 (CH$_2$); 1.51(CH$_2$); 2.14 (CH$_2$); 1.73 (m, ring, 1.2); 2.21(ring 3H); 2.05 (ring 4H); 7.39 (1H, NH); $^{13}$C-NMR (CDCl$_3$): δ13.4(CH$_3$); 21.9 (CH$_2$); 27.3(CH$_2$); 35.4(CH$_2$); 22.7[2C(1.2)]; 38.4 [2C (3.4)]; 54.6(C quaternary); 121.2(CN); 173.7(NH-CO); IR ν max: 2238(CN); 1654 (CO); 3304(NH); MS: (m/z) 194 (M+H), 165, 152, 137, 111, 102, 85, 51, 41, 29.

EXAMPLE 2

1-cyano-1-n-pentanoylaminocyclopentane 11.0 g (0.1mol) of 1-amino-1-cyanocyclopentane and 20.5 g (0.11 mol) of valeric anhydride were refluxed for 3 hours. The reaction mixture was evaporated under vacuo to constant weight. The resulting 19.3 g oil (98.5%) was identical with the product obtained in Example 1.

EXAMPLE 3

1-cyano-1-n-pentanoylaminocyclopentane 11.0 g (0.1 mol) of 1-amino-1-cyanocyclopentane and 20.4 g (0.2 mol) of valeric acid were placed in an apparatus equipped with water-separatory distillation head and boiled until 1.8 ml of water distilled off. The reaction mixture was then evaporated in fine vacuum to constant weight.

19.1 g (97.4%) of oily product was obtained which was identical with the product obtained in Example 1.

EXAMPLE 4

1-cyano-1-n-pentanoylaminocyclopentane 11.0 g (0.1 mol) of 1-amino-1-cyanocyclopentane, 13.9 g (0.12 mol) of methyl valerate and 1.0 g sodiumn methylate were boiled for 16 hours. The volatile products were then distilled off in vacuo. To the residue 50 ml of water was added, the pH was adjusted to neutral by the addition of acetic acid and the mixture was extracted with 70 ml followed by 2x50 ml of dichloroethane. The combined organic phases were dried over sodium sulfate and evaporated in vacuo to constant weight.

13.1 g (66.8%) of oily product was obtained which was identical with the product obtained in Example 1.

EXAMPLE 5

1-cyano-1-formylaminocyclopentane 11.0 g (0.1 mol) of 1-amino-1-cyanocyclopentane and 10 ml of 85% formic acid were placed in an apparatus equipped with water-separatory distillation head and boiled for 3 hours. The reaction mixture was then evaporated to constant weight in vacuo.

12.4 g (90%) of oily product was obtained which on investigation by GC-MS gave the following fragments of the title product M: 138, 137, 123, 111, 110, 109, 93 81, 68, 66, 54, 46, 41 (R$_t$: 10.7')

EXAMPLE 6

2-butyl-1,3-diaza-spiro [4.4] non-1-en-4-one monohydrochloride

To the solution made of 11.0 g (0.1 mol) of 1-amino-1-cyanocyclopentane and 12.2 g (0.12 mol) of triethylamine in 80 ml of toluene, 13.0 g (0.1 mol) of valeroyl chloride was added at 30° C. After the addition the mixture was stirred at 60° C. for 1 hour, then it was cooled and washed three times with water. The phases were separated and to the organic phase at first 25 g of 20 w/v % sodium hydroxide solution and 7 g of tetrabutyl ammonium hydrogen sulfate, then at 10–15° C. 40 g of 30–35 w/v % hydrogen peroxide solution were added. The reaction mixture was heated to 25–30° C. and was stirred at that temperature for 2 hours. The mixture was then heated to 60° C. and the phases were separated again. To the toluene phase the solution of 3 g of sodium in 30 ml methanol was added and the mixture was heated to reflux temperature to distill out the solvent and the volatile components. The concentration was continued until the mixture was stirrable. To the resulting product 100 ml of acetone was added, the mixture was filtered and the pH of the filtrate was adjusted to 1–2 with conc. hydrochloric acid. The precipitated product was filtered off and dried to obtain 14 g of the title compound, yield 60.8%.

IR: 3600-2200: vibr, NH; 1779: γ c=o; 1642 γ c, 1517: δ NH (IRFT Perkin Elmer); 1H NMR: 0.9 ppm T (CH$_3$); 1.34 ppm S (CH$_2$); 1.73 ppm Q (CH$_2$); 1.78–2.01 ppm M cyclopentane (CH$_2$); 2.78 ppm T (CH$_2$); 9–15 ppm (NH, N) MS: 194, 179, 166, 165, 152, 124, 84, 83, 54, 41 VRK: Eluent: chloroform: methanol=6:1, TLC plate: Kieselgel GF254 Detection: I$_2$ vapor Rf=0.64

EXAMPLE 7

2-butyl-1,3-diaza-spiro [4.4] non-1-en-4-one monohydrochloride

The procedure as described in Example 6 was followed, but 5 g of cetyltrimethylammonium hydroxide was applied. 17 g of the title compound was obtained (yield 74%). Physical characteristics of the product are identical with those of the product obtained in Example 6.

EXAMPLE 8

2-butyl-1,3-diaza-spiro [4.4] non-1-en-4-one monohydrochloride

The procedure as described, in Example 6 was followed, but to promote the heterogen phase reaction the mixture was stirred with sonicator. 14 g of the title compound was obtained (yield 61%). Physical characteristics of the product are identical with those of the product obtained in Example 6.

EXAMPLE 9

2-butyl-1,3-diaza-spiro [4.4] non-1-en-4-one monohydrochloride

The procedure as described in Example 6. was followed, but the anxino-1-cyanocyclopentane was dissolved in methyl terc.-butyl ether, instead of toluene and the separation of the aqueous layer was performed at 50–55° C. 14 g of the title compound was obtained (yield 61%). Physical characteristics of the product are identical with those of the product obtained in Example 6.

EXAMPLE 10

2-butyl-1,3-diaza-spiro [4.4] non-1-en4-one monohidrochloride

To the solution of 11.0 g (0.1 mol) of 1-amino-1-cyanocyclopentane in 110 g of toluene 12.2 g (0.12 mol) of triethylamine was added and to this solution 13.0 g (0.1 mol) of valeroyl chloride was added dropwise, under cooling, at 25–30° C. After 10 minutes the temperature was raised to 60° C. and the mixture was stirred at that temperature for 1 hour. The reaction mixture was then cooled to 20° C. and it was extracted consecutively with: 50 ml of water, 50 ml of 2% hyrochloric acid solution and 30 ml of water. The toluene solution was evaporated to constant weight in vacuo, to the residue were added at first the solution of 3 g (0.056 mol) of potassium hydroxide in 50 ml of methanol, then under cooling, at a temperature between 20–30° C. 30 ml of 30% hydrogenperoxide solution. External cooling was then discontinued and the temperature was allowed to raise 50–60° C. After approximately 30 minutes the temperature began to decrease. At that point the solution of 17 g (0.314 mol) of potassium hydroxide in 17 ml of water was added to it, and the mixture was heated under reflux conditions for 1 hour. The reaction was then freezed by the addition of 20 g of ammonium chloride and methanol was distilled out by raising the inner temperature to 85° C. The reaction mixture was extracted with 50 and 2×30 ml of toluene, the combined organic phases were evaporated in vacuo, the residue was dissolved in 5-fold amount of acetone, the resulting solution was filtered, its pH was adjusted to 1–2 by the addition of conc. hydrochloric acid solution. The suspension thus obtained was stirred for 30 minutes, cooled to 0° C., the crystals were filtered off, washed with cold acetone and dried to obtain 18 g of the title compound (yield 78.3%). Physical characteristics of the product were identical with those of the product obtained in Example 6.

EXAMPLE 11

2-butyl-1,3-diaza-spiro [4.4] non-1-en-4-one monohydrochloride

The mixture of 19.6 g of 1-amino-1-n-pentanoylaminocyclopentane, 200 ml of water, 300 ml of acetone and 36.9 g of sodium perkarbonate (0.3 equivalent hydrogenperoxide) was stirred for 3 hours at 50° C. Acetone was removed in vacuo, to the residue 50 ml of methanol and 15.0 g (0.28 mol) of potassium hydroxide was added and the solution thus obtained was refluxed for 2 hours. To the reaction mixture 15 g of ammonium chloride was added and after 10 minutes of stirring methanol was distilled off in vacuo. The residue was extracted with 70 ml and 2×50 ml of toluene, the combined organic phases were evaporated, the residue was dissolved in 100 ml of acetone, after filtration the pH of the solution was adjusted to 1–2 with concentrated hydrochloric acid and the resulting suspension was cooled, filtered, the crystals were washed with cold acetone and dried.

16.1 g of title compound was obtained, yield 70%. Physical characteristics of the product were identical with those of the product obtained in Example 6.

EXAMPLE 12

2-butyl-1,3-diaza-spiro [4.4] non-1-en-4-one monohydrochloride 19.6 g (0.1 mol) of 1-cyano-1-n-pentanoylaminocyclopentane was dissolved in 70 ml of ethanol, to the solution 3.7 g (0.05 mol) of calcium hydroxide, and then, dropwise, under cooling 25 ml of 30% hydrogenperoxide solution. The temperature was allowed to raise to 50–60° C., without external cooling. After 1 hour of stirring the reaction mixture was filtered, to the filtrate solution 10 g of freshly activated VARION AD® ion-exchange resin was added, after 2 hours of reflux the resin was filtered off. The filtrate was evaporated to constant weight in vacuo, to the residue 100 ml of acetone was added. The pH of the resulting solution was adjusted to 1–2 with dry hydrogen chloride gas, the suspension thus obtained was cooled to 0° C., the crystals were filtered off, washed with cold acetone and dried.

15.7 g of title compound was obtained,. yield: 68.3%. Physical characteristics of the product were identical with those of the product obtained in Example 6.

EXAMPLE 13

1,3-diaza-spiro [4.4] non-1-en-4-one monohydrochloride

To the suspension of 13.8 g (0.1 mol) of 1-cyano-1-formylaminocyclopentane 70 ml of n-butanol and 5.0 g (0.05 mol) of calcium carbonate was added, dropwise 20 ml of 30% hydrogenperoxide solution, in a pace that the temperature of the mixture slowly enhances and does not exceed 50° C. After 1 hour of stirring the reaction mixture was filtered. To the filtrate solution 12.0 g (0.3 mol) of sodium hydroxide was added and after 30 minutes of reflux the reaction was freezed by the addition of 12 g of ammonium chloride. To the reaction mixture water was added, in an amount that the precipitated salt dissolves The solution was then extracted with 70 ml and 2×50 ml of methyl terc.butyl ether. After drying over sodium sulfate the solution was saturated with dry hydrogen chloride gas, the resulting suspension was cooled, the crystals were filtered off, washed with dry acetone and dried.

9.0 g of title compound was obtained, yield: 52%. Mp: 219–221° C. (decomp.); IR: 1663 cm$^{-1}$ C=N 1739 cm$^{31\ 1}$ C=O 3197 cm$^{31\ 1}$ H(NH) MH$^+$: 139.

What is claimed is:

1. A process for the preparation of compounds of general formula (I):

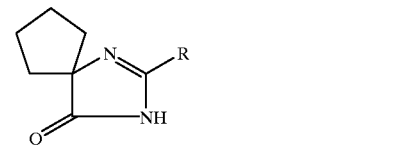

(I)

wherein R means hydrogen atom or $C_{2-6}$ alkyl group characterized in that a) the compound of general formula (III):

(III)

is reacted with a compound of general formula (IV):

(IV)

wherein the meaning of R is defined above, and X means halogen atom or $C_{1-5}$ alkoxy group or hydroxyl group, and the resulting compound of general formula (II):

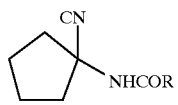
(II)

wherein the meaning of R is defined above, is transformed in the presence of an oxidizing agent in a reaction medium with pH above 7, into the compound of general formula (I), wherein the meaning of R is as defined above, or b) the compound of formula (III) is reacted with an anhydride of general formula (V):

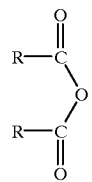
(V)

wherein the meaning of R is the same as defined above, and the resulting compound of general formula (II), wherein the meaning of R is as given above, is transformed in the presence of an oxidizing agent, in a reaction medium with pH above 7, into the compound of general formula (I), or c) a compound of general formula (II), wherein the meaning of R is the same as defined above, is transformed in the presence of an oxidizing agent, in a reaction medium with pH above 7, into the compound of general formula (I), and optionally, the resulting compounds of general formula (I), before or after isolation, are transformed into acid addition salts, or the compounds of general formula (I) are liberated from their acid addition salts, characterized in that the reaction is carried out in homogeneous phase.

2. A process for the preparation of compounds of general formula (I):

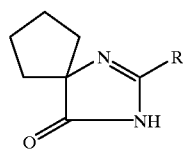
(I)

wherein R means hydrogen atom or $C_{2-6}$ alkyl group characterized in that a) the compound of general formula (III):

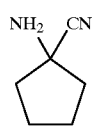
(III)

is reacted with a compound of general formula (IV):

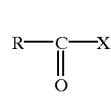
(IV)

wherein the meaning of R is defined above, and X means halogen atom or $C_{1-5}$ alkoxy group or hydroxyl group, and the resulting compound of general formula (II):

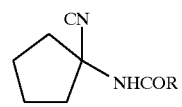
(II)

wherein the meaning of R is defined above, is transformed in the presence of an oxidizing agent in a reaction medium with pH above 7, into the compound of general formula (I), wherein the meaning of R is as defined above, or b) the compound of formula (III) is reacted with an anhydride of general formula (V):

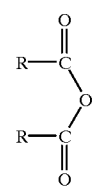
(V)

wherein the meaning of R is the same as defined above, and the resulting compound of general formula (II), wherein the meaning of R is as given above, is transformed in the presence of an oxidizing agent, in a reaction medium with pH above 7, into the compound of general formula (I), or c) a compound of general formula (II), wherein the meaning of R is the same as defined above, is transformed in the presence of an oxidizing agent, in a reaction medium with pH above 7, into the compound of general formula (I), and optionally, the resulting compounds of general formula (I), before or after isolation, are transformed into acid addition salts, or the compounds of general formula (I) are liberated from their acid addition salts, characterized in that the reaction is carried out in heterogeneous phase.

3. A process for the preparation of compounds of general formula (I):

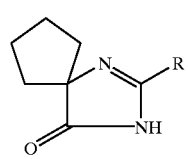
(I)

wherein R means hydrogen atom or $C_{2-6}$ alkyl group characterized in that a) the compound of general formula (III):

(III)

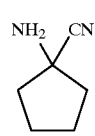

is reacted with a compound of general formula (IV):

(IV)

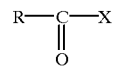

wherein the meaning of R is defined above, and X means halogen atom or $C_{1-5}$ alkoxy group or hydroxyl group, and the resulting compound of general formula (II):

(II)

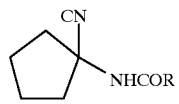

wherein the meaning of R is the same as given in claim 1, is transformed in the presence of an oxidizing agent in a reaction medium with pH above 7, into the compound of general formula (I), wherein the meaning of R is as defined above, or b) the compound of formula (III) is reacted with an anhydride of general formula (V):

(V)

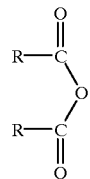

wherein the meaning of R is the same as defined above, and the resulting compound of general formula (II), wherein the meaning of R is as given above, is transformed in the presence of an oxidizing agent, in a reaction medium with pH above 7, into the compound of general formula (I), or c) a compound of general formula (II), wherein the meaning of R is the same as defined above, is transformed in the presence of an oxidizing agent, in a reaction medium with pH above 7, into the compound of general formula (I), and optionally, the resulting compounds of general formula (I), before or after isolation, are transformed into acid addition salts, or the compounds of general formula (I) are liberated from their acid addition salts, characterized in that as for oxidizing agents hydrogen peroxide or organic or inorganic peroxi-compounds are applied.

4. The process according to claim 2, characterised in that as for oxidising agents peroxo-carbonates, peroxo-borates, peroxo-disulfates are employed.

5. A process for the preparation of compounds of general formula (I):

(I)

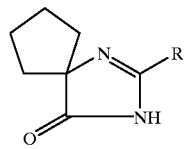

wherein R means hydrogen atom or $C_{2-6}$ alkyl group characterized in that a) the compound of general formula (III):

(III)

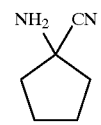

is reacted with a compound of general formula (IV):

(IV)

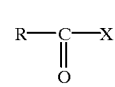

wherein the meaning of R is defined above, and X means halogen atom or $C_{1-5}$ alkoxy group or hydroxyl group, and the resulting compound of general formula (II):

(II)

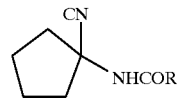

wherein the meaning of R is defined above, is transformed in the presence of an oxidizing agent in a reaction medium with pH above 7, into the compound of general formula (I), wherein the meaning of R is as defined above, or b) the compound of formula (III) is reacted with an anhydride of general formula (V):

(V)

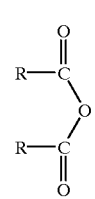

wherein the meaning of R is the same as defined above, and the resulting compound of general formula (II), wherein the meaning of R is as given above, is transformed in the presence of an oxidizing agent, in a reaction medium with pH above 7, into the compound of general formula (I), or c) a compound of general formula (II), wherein the meaning of R is the same as defined above, is transformed in the presence of an oxidizing agent, in a reaction medium with pH above 7, into the compound of general formula (I), and optionally, the resulting compounds of general formula (I), before or after isolation, are transformed into acid addition salts, or the compounds of general formula (I) are liberated from their acid addition salts, characterized in that the compounds of general formula (II) are transformed into the compounds of general formula (I) in the presence of an oxidizing agent and base.

6. The process according to claim 5, characterised in that as for base, alkali alcoholates, alkali metal hydroxides, alkali metal carbonates or ion-exchange resins are used.

7. A process for the preparation of compounds of general formula (I):

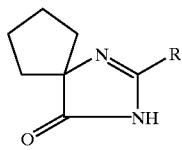
(I)

wherein R means hydrogen atom or $C_{2-6}$ alkyl group characterized in that a) the compound of general formula (III):

(III)

is reacted with a compound of general formula (IV):

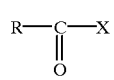
(IV)

wherein the meaning of R is defined above, and X means halogen atom or $C_{1-5}$ alkoxy group or hydroxyl group, and the resulting compound of general formula (II):

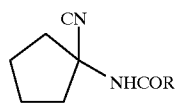
(II)

wherein the meaning of R is defined above, is transformed in the presence of an oxidizing agent in a reaction medium with pH above 7, into the compound of general formula (I), wherein the meaning of R is as defined above, or b) the compound of formula (III) is reacted with an anhydride of general formula (V):

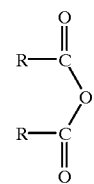
(V)

wherein the meaning of R is the same as defined above, and the resulting compound of general formula (II), wherein the meaning of R is as given above, is transformed in the presence of an oxidizing agent, in a reaction medium with pH above 7, into the compound of general formula (I), or c) a compound of general formula (II), wherein the meaning of R is the same as defined above, is transformed in the presence of an oxidizing agent, in a reaction medium with pH above 7, into the compound of general formula (I), and optionally, the resulting compounds of general formula (I), before or after isolation, are transformed into acid addition salts, or the compounds of general formula (I) are liberated from their acid addition salts, characterized in that in the reaction taking place between the compound of formula (III) and a compound of general formula (IV) or (V) an acid binding agent is used.

8. The process according to claim 7, characterised in that as for acid binding agent amines, alkali-earth metal carbonates, alkali-earth metal carbonates or alkali-earth metal oxides are applied.

9. A process for the preparation of compounds of general formula (I):

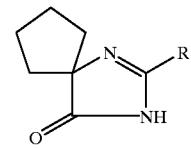
(I)

wherein R means hydrogen atom or $C_{2-6}$ alkyl group characterized in that a) the compound of general formula (III):

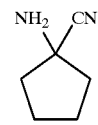
(III)

is reacted with a compound of general formula (IV):

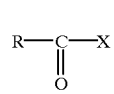
(IV)

wherein the meaning of R is defined above, and X means halogen atom or $C_{1-5}$ alkoxy group or hydroxyl group, and the resulting compound of general formula (II):

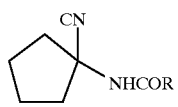

(II)

wherein the meaning of R is defined above, is transformed in the presence of an oxidizing agent in a reaction medium with pH above 7, into the compound of general formula (I), wherein the meaning of R is as defined above, or b) the compound of formula (III) is reacted with an anhydride of general formula (V):

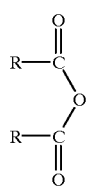

(V)

wherein the meaning of R is the same as defined above, and the resulting compound of general formula (II), wherein the meaning of R is as given above, is transformed in the presence of an oxidizing agent, in a reaction medium with pH above 7, into the compound of general formula (I), or c) a compound of general formula (II), wherein the meaning of R is the same as defined above, is transformed in the presence of an oxidizing agent, in a reaction medium with pH above 7, into the compound of general formula (I), and optionally, the resulting compounds of general formula (I), before or after isolation, are transformed into acid addition salts, or the compounds of general formula (I) are liberated from their acid addition salts, characterized in that as for solvents aromatic hydrocarbones, halogenated aliphatic hydrocarbones, aliphatic ethers, alcohols, as well as homogeneous or heterogeneous aqueous solvent systems formed between the above solvents and water, are applied.

10. The process according to claim 2, characterised in that phase transfer catalyst and/or dissolution transfer is used.

11. The process according to claim 10, characterised in that as for phase transfer alkyl ammonium hydrogen sulfates, hydrogen halogenides or hydroxides, and as for dissolution transfer longer chain alcohols are used.

12. A process for the preparation of compounds of general formula (I):

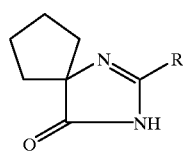

(I)

wherein R means hydrogen atom or $C_{2-6}$ alkyl group characterized in that a) the compound of general formula (III):

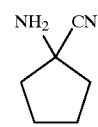

(III)

is reacted with a compound of general formula (IV):

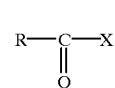

(IV)

wherein the meaning of R is defined above, and X means halogen atom or $C_{1-5}$ alkoxy group or hydroxyl group, and the resulting compound of general formula (II):

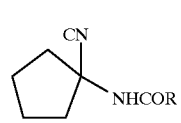

(II)

wherein the meaning of R is defined above, is transformed in the presence of an oxidizing agent in a reaction medium with pH above 7, into the compound of general formula (I), wherein the meaning of R is as defined above, or b) the compound of formula (III) is reacted with an anhydride of general formula (V):

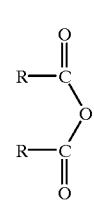

(V)

wherein the meaning of R is the same as defined above, and the resulting compound of general formula (II), wherein the meaning of R is as given above, is transformed in the presence of an oxidizing agent, in a reaction medium with pH above 7, into the compound of general formula (I), or c) a compound of general formula (II), wherein the meaning of R is the same as defined above, is transformed in the presence of an oxidizing agent, in a reaction medium with pH above 7, into the compound of general formula (I), and optionally, the resulting compounds of general formula (I), before or after isolation, are transformed into acid addition salts, or the compounds of general formula (I) are liberated from their acid addition salts, characterized in that the reaction is carried out without isolating the compounds of general formula (II).

* * * * *